(12) United States Patent
Indo et al.

(10) Patent No.: US 7,687,770 B2
(45) Date of Patent: Mar. 30, 2010

(54) METHODS AND APPARATUS FOR MULTI DIMENSION FLUORESCENCE SPECTRUM MEASUREMENT DOWNHOLE

(75) Inventors: Kentaro Indo, Edmonton (CA); Albert Ballard Andrews, Wilton, CT (US); Stephane Vannuffelen, Tokyo (JP); Tsutomu Yamate, Yokohama (JP); Toru Terabayashi, Sagamihara (JP); Hideki Kinjo, Sagamihara (JP); Oliver C. Mullins, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/625,276

(22) Filed: Jan. 19, 2007

(65) Prior Publication Data
US 2008/0173805 A1     Jul. 24, 2008

(51) Int. Cl.
*G01V 5/08* (2006.01)
(52) U.S. Cl. .................................... 250/269.1
(58) Field of Classification Search .... 250/269.1–169.8
See application file for complete search history.

(56) References Cited
U.S. PATENT DOCUMENTS

| | | | |
|---|---|---|---|
| 2,206,922 A | | 7/1940 | Smith |
| 2,346,481 A | | 4/1944 | Garrison |
| 3,617,746 A | * | 11/1971 | Janssen et al. ............... 250/265 |
| 5,049,738 A | * | 9/1991 | Gergely et al. ............... 250/301 |
| 5,084,617 A | * | 1/1992 | Gergely ....................... 250/253 |
| 5,219,693 A | * | 6/1993 | Akao et al. .................... 430/72 |
| 5,859,430 A | | 1/1999 | Mullins et al. |
| 5,912,459 A | | 6/1999 | Mullins et al. |
| 5,939,717 A | | 8/1999 | Mullins |
| 6,140,637 A | | 10/2000 | Mullins et al. |
| 6,268,603 B1 | | 7/2001 | Mullins et al. |
| 6,378,627 B1 | * | 4/2002 | Tubel et al. ................... 175/24 |
| 6,465,775 B2 | | 10/2002 | Mullins et al. |
| 6,476,384 B1 | | 11/2002 | Mullins et al. |
| 7,002,142 B2 | * | 2/2006 | Mullins et al. ........... 250/269.1 |
| 7,084,392 B2 | * | 8/2006 | DiFoggio et al. ......... 250/269.1 |

(Continued)

FOREIGN PATENT DOCUMENTS

GB     2399971     9/2004

(Continued)

OTHER PUBLICATIONS

Brown et al, "Development of a tunable LED-based calorimetric source", Aug. 2002, Journal of Research of the National Institute of Standards and Technology, vol. 107, No. 4, pp. 363-371.*

(Continued)

*Primary Examiner*—David P Porta
*Assistant Examiner*—Kiho Kim
(74) *Attorney, Agent, or Firm*—Matthias Abrell; Jaime Castano; Dale Gaudier

(57) ABSTRACT

Some principles described herein contemplate implementation of downhole imaging for the characterization of formation fluid samples in situ, as well as during flow through production tubing, including subsea flow lines, for short term investigation, permanent, and/or long term installations. Various methods and apparatus described herein may facilitate downhole testing. For example, some embodiments facilitate multi-dimensional fluorescence spectrum measurement testing downhole.

24 Claims, 9 Drawing Sheets

U.S. PATENT DOCUMENTS

| | | | |
|---|---|---|---|
| 2004/0000636 A1 | 1/2004 | Mullins et al. | |
| 2004/0007665 A1* | 1/2004 | DiFoggio et al. | 250/269.1 |
| 2004/0104355 A1 | 6/2004 | DiFoggio et al. | |
| 2005/0012036 A1* | 1/2005 | Tubel et al. | 250/227.14 |
| 2005/0067562 A1* | 3/2005 | Dong et al. | 250/269.1 |
| 2006/0175547 A1* | 8/2006 | DiFoggio et al. | 250/269.1 |
| 2006/0243047 A1* | 11/2006 | Terabayashi et al. | 73/152.55 |
| 2007/0068242 A1* | 3/2007 | DiFoggio | 73/152.55 |
| 2007/0117215 A1* | 5/2007 | Davis et al. | 436/172 |
| 2007/0171414 A1* | 7/2007 | Vannuffelen et al. | 356/328 |
| 2008/0265177 A1* | 10/2008 | Connally et al. | 250/461.2 |

FOREIGN PATENT DOCUMENTS

| | | |
|---|---|---|
| WO | 2004/102155 | 11/2004 |

OTHER PUBLICATIONS

O.C. Mullins, "Optical interrogation of aromatic moieties in crude oils and asphaltenes", Chap. 2 of Structures and Dynamics of Asphaltenes, Plenum Pub. Co. New York, (1998).

H. Groenzin, O.C. Mullins, "Asphaltene Molecular Size and Weight by Time-Resolved Fluorescence Depolarization", Chap. 2 of Asphaltenes, Heavy Oils, and Petroleomics, Springer, (2007).

Y. Zhu, O.C. Mullins, "Temperature Dependence of Fluorescence of Crude Oils and Related Compounds", Energy & Fuels 1992, 6, pp. 545-552.

X. Wang, O.C. Mullins, "Fluorescence Lifetime Studies of Crude Oils", Applied Spectrosc., vol. 48, No. 8, 1994, pp. 977-984.

T.D. Downare, O.C. Mullins, X. Wu, "Optimization of a Fluorescence Detection System for the Characterization of Solids", Applied Spectrosc., vol. 48, No. 12, 1994, pp. 1483-1490.

T.D. Downare, O.C. Mullins, "Visible and Near-Infrared Fluorescence of Crude Oils", Applied Spectrosc., vol. 49, No. 6, 1995, pp. 754-764.

J.R. Bezouska, J.Wang, O.C. Mullins, "Origin of Limestone Fluorescence", Applied Spectrosc., vol. 52, No. 12, 1998, pp. 1606-1613.

H. Groenzin, O.C. Mullins, W.W. Mullins, "Resonant Fluorescence Quenching of Aromatic Hydrocarbons by Carbon Disulfide", J. Phys, Chem. A 1999, 103, pp. 1504-1508.

H. Groenzin, O.C. Mullins, "Asphaltene Molecular Size and Structure", J.Phys. Chem. A 1999, 103, pp. 11237-11245.

H. Groenzin, O.C. Mullins, S. Eser, J. Mathews, M-G. Yang, D. Jones, "Molecular Size of Asphaltene Solubility Fractions", Energy & Fuels 2003, 17, pp. 498-503.

C. Canuel, S. Badre, H. Groenzin, M. Berheide, O.C. Mullins, "Diffusional Fluorescence Quenching of Aromatic Hydrocarbons", Applied Spectrosc., vol. 57, No. 5, 2003, pp. 538-544.

G. Andreatta, C.C. Goncalves, G. Buffin, N. Bostrom, C.M. Quintella, F. Arteaga-Larios, E.Perez, O.C. Mullins, "Nanoaggregates and Structure-Function Relations in Asphaltenes", Energy & Fuels 2005, 19, pp. 1282-1289.

A.B. Andrews, R.E. Guerra, O.C. Mullins, P.N. Sen, "Diffusivity of Asphaltene Molecules by Fluorescence Correlation Spectroscopy", J. Phys. Chem. A 2006, 110, pp. 8093-8097.

S.S. Betancourt, G. Fujisawa, O.C. Mullins, K.O. Eriksen, C. Dong, J. Pop, A. Carnegie, "Exploration Applications of Downhole Measurement of Crude Oil Composition and Fluorescence", SPE #87011, Asia. 2003.

M.N. Hasham, E.C. Thomas, O.C. Mullins, "Determination of Producible Hydrocarbon Type and Oil Quality in Wells Drilled with Synthetic Oil-Based Muds", SPE 39093, Proceedings of the Annual SPE Conference 1997, San Antonio TX.

* cited by examiner

METHODS AND APPARATUS FOR MULTI DIMENSION FLUORESCENCE SPECTRUM MEASUREMENT DOWNHOLE

FIELD

The present disclosure relates generally to methods and systems for investigating subterranean formation fluids. More particularly, some aspects of this disclosure are directed to methods and systems for spectral imaging to characterize downhole fluids.

BACKGROUND

Fluid characterization is very important to the assessment of economic viability for a hydrocarbon-bearing reservoir formation. Some wireline tools such as Schlumberger's MDT (Modular Dynamic Tester) are used to sample formation fluids, store it in a set of bottles, and retrieve it to surface while keeping the fluid pressurized. Such samples are known as live fluids. These live fluids are then sent to an appropriate laboratory to be characterized. Characterization of the fluids may include composition analysis, fluid properties and phase behavior.

Understanding reservoir fluid phase behavior is key to proper planning and development of the respective fields and design of the production system. Understanding reservoir fluid phase behavior involves conducting a number of very important measurements on the fluid at realistic reservoir and production conditions. In most cases, changes in temperature (T) and pressure (P) of the formation fluid lead to phase changes, including phase separation (e.g., liquid-vapor, liquid-solid, liquid-liquid, vapor-liquid etc.), and phase recombination. For example, while most hydrocarbons exist as a single phase at initial reservoir conditions (i.e., composition, pressure, and temperature), they often undergo reversible (and possibly some irreversible) multi-phase changes due to pressure, composition and/or temperature reduction during production and flow to the surface facilities.

Liquid-Solid-Vapor phase boundaries are typically measured at a laboratory using state-of-the-art-technologies, such as Schlumberger's pressure-volume-temperature (PVT) unit coupled to Schlumberger's laser-based Solids Detection System (SDS) and Schlumberger's high-pressure microscope (HPM). Detailed descriptions of these state-of-the art technologies and their applications for the study of phase behavior and flow assurance of petroleum fluids have been published and are known to those of skill in the art.

However, one current trend in the industry is to perform more and more analysis of the formation and the formation fluid properties directly downhole to avoid the difficulties associated with sample preservation when lifted uphole and delays associated with sample transportation and analysis in a remote laboratory. Tools like Schlumberger's MDT can, for example, be retrofitted with a spectrometer module such as a Live Fluid Analyser or Gas Condensate Analyser in order to provide basic information on the fluid composition (Gas-to-oil ratio (GOR), water content, basic crackdown of hydrocarbon fractions ($C_1$, $C_2$-$C_5$, $C_6$+)). These measurements are performed by infrared (IR) absorption spectroscopy.

Nevertheless, current measurements of certain downhole characteristics do not facilitate full analysis of the formation and fluids, especially in situ. Fluorescence measurements downhole as discussed herein may be used to more fully characterize formations and formation fluids. In addition, U.S. Patent Application Publication Number 2004/0000636 assigned to Schlumberger Technology Corporation and invented by Oliver Mullins et al. discusses determining dew precipitation onset pressure in a sample located downhole in an oilfield reservoir, which may include measuring 1D fluorescence.

Further, while there has been some use of video imaging downhole in wireline tools, current technology is generally limited to applications related to production logging. Most current downhole imaging is dedicated to borehole wall imaging and has low spatial resolution (although commonly-owned U.S. patent application Ser. No. 11/204,134 discusses additional imaging capability). DHV International, for example, provides downhole video services to the oil and gas industry for diagnosis of borehole problems such as fishing out lost tools, mechanical inspection, and fluid entry surveys. There is room to improve methods and systems to more fully characterize formation fluids downhole.

SUMMARY

The present specification may meet the above-described needs and others. In one embodiment, the present disclosure provides a method comprising providing a downhole testing tool, deploying the downhole testing tool into a borehole, and performing a multi-dimensional fluorescence spectrum measurement downhole. In this, the disclosure herein contemplates applications in wireline tools, drilling and measuring tools, permanent monitoring, production logging, among others, with deployment modes that include conventional wireline and drilling systems, and slickline, coiled tubing, clamping devices, etc.

In one embodiment, two of the multi-dimensional fluorescence spectrum measurements comprise wavelength of excitation light and fluorescence spectrum. In one embodiment, the multi-dimensional fluorescence spectrum measurements comprise characterization of an aromatic fraction of a live oil. In one embodiment, two of the multi-dimensional fluorescence spectrum measurements comprise fluorescence relaxation time and fluorescence spectrum. In one embodiment, performing the multi-dimensional fluorescence spectrum measurement comprises two dimensional fluorescence imaging with a charged-coupled device (CCD) or a complementary metal oxide semiconductor (CMOS) camera. The method may include communicating the multi-dimensional fluorescence spectrum measurement uphole. One embodiment of the method comprises performing the multi-dimensional fluorescence spectrum measurement downhole at multiple boreholes, comparing the multi-dimensional fluorescence spectrum measurements at the multiple boreholes, and determining connectivity between the multiple boreholes based on the comparing of the multi-dimensional fluorescence spectrum measurements. In one embodiment, the downhole testing tool further comprises a pressure-volume control unit. Some embodiments of the downhole testing tool comprise a portion of a wireline tool. In one embodiment, the downhole testing tool is permanently installed downhole and in fluid communication with a production line. Some embodiments further comprise performing a multi-dimensional fluorescence spectrum measurement in a lab on a same fluid measured downhole, and comparing the multi-dimensional fluorescence spectrum measurement of the lab with multi-dimensional fluorescence spectrum measurement performed downhole. The comparison may be used to establish a clean chain of custody.

One aspect provides a method of identifying subterranean fluids. The subterranean or downhole fluids may be formation fluids, drilling muds, or other fluids. The method comprises characterizing a formation fluid sample downhole according to multi-dimensional fluorescence spectrum measurements. In one embodiment, two of the multi-dimensional fluorescence spectrum measurements comprise wavelength of excitation light and fluorescence spectrum. In another embodiment, two of the multi-dimensional fluorescence spectrum measurements comprise fluorescence relaxation time and fluorescence spectrum. In another embodiment, performing the multi-dimensional fluorescence spectrum measurement comprises two dimensional fluorescence imaging with a charged-coupled device (CCD) or a complementary metal oxide semiconductor (CMOS) camera. In one embodiment, a light source and the camera comprise a transmission imaging configuration. In one embodiment, a light source, a reflector, and a camera comprise a back-scattered imaging configuration.

One aspect provides a method of identifying subterranean formation fluids, comprising providing a downhole testing tool having an optical fluid analyzer, deploying the downhole testing tool into a borehole, exciting an energy state of the formation fluids adjacent to the optical fluid analyzer above a ground state, measuring fluorescence light emitted by the formation fluids in a relaxation process from an excited state to the ground state, and plotting fluorescence spectra as a function of time. One embodiment further comprises comparing plots of fluorescence spectra as a function of time with samples from various boreholes. One embodiment further comprises comparing plots of fluorescence spectra as a function of time with samples of known properties. One embodiment further comprises comparing plots of fluorescence spectra as a function of time with samples from various boreholes, and determining similarities between the plots of the samples from the various boreholes to anticipate well connectivity.

One embodiment provides a downhole apparatus. The downhole apparatus comprises a downhole lab module. The downhole lab module comprises a sample flow line, a sample cell in fluid communication with the sample flow line, the sample cell comprising at least one optical or transparent window, a light source adjacent to the sample cell, a spectrometer for detecting fluorescence, and a set of instructions, that, when executed, perform multi-dimensional fluorescence spectrum measurements downhole. One embodiment further comprises a set of instructions that, when executed, excite an energy state of the formation fluids adjacent to the optical fluid analyzer above a ground state, measure fluorescence light emitted by the formation fluids in a relaxation process from an excited state to the ground state, and plot fluorescence spectra as a function of time. One embodiment further comprises a set of instructions that, when executed, excite an energy state of the formation fluids adjacent to the optical fluid analyzer above a ground state, measure fluorescence light emitted by the formation fluids in a relaxation process from an excited state to the ground state, and plot wavelength of excitation light versus fluorescence spectrum. One embodiment further comprises a camera capable of 2D fluorescence imaging of formations downhole.

One embodiment provides a downhole apparatus comprising a downhole lab module, the downhole lab module comprising a cell having an optical window in contact with a downhole formation, a light source adjacent to the cell, a spectrometer for detecting fluorescence emitted from the formation, and a set of instructions, that, when executed, perform multi-dimensional fluorescence spectrum measurements downhole of the formation.

One embodiment includes a method comprising providing a downhole testing tool, deploying the downhole testing tool into a borehole, and performing a multi-dimensional fluorescence spectrum measurement downhole. Two of the multi-dimensional fluorescence spectrum measurements comprise fluorescence relaxation time and fluorescence spectrum.

One aspect provides a method comprising providing a downhole testing tool, deploying the downhole testing tool into a borehole, and performing a multi-dimensional fluorescence spectrum measurement downhole, where the performing the multi-dimensional fluorescence spectrum measurement comprises two dimensional fluorescence imaging with a charged-coupled device (CCD) or a complementary metal oxide semiconductor (CMOS) camera.

One aspect provides a method, comprising providing a downhole testing tool, deploying the downhole testing tool into a borehole, and performing a multi-dimensional fluorescence spectrum measurement downhole, the multiple fluorescence spectrum measurement comprising one of: fluorescence relaxation time and fluorescence spectrum, two dimensional fluorescence imaging with a charged-coupled device (CCD) or a complementary metal oxide semiconductor (CMOS) camera.

One embodiment provides a downhole apparatus comprising a downhole lab module, the downhole lab module comprising a sample flow line, a sample cell in fluid communication with the sample flow line, the sample cell comprising at least one optical window, a light source adjacent to the sample cell, a spectrometer for detecting fluorescence, a set of instructions, that, when executed: excite an energy state of the formation fluids adjacent to the optical fluid analyzer above a ground state, measure fluorescence light emitted by the formation fluids in a relaxation process from an excited state to the ground state, and plot fluorescence spectra as a function of time.

One embodiment provides a downhole apparatus comprising a downhole lab module, the downhole lab module comprising a sample flow line, a sample cell in fluid communication with the sample flow line, the sample cell comprising at least one optical window, a light source adjacent to the sample cell, a spectrometer for detecting fluorescence, a camera capable of 2D fluorescence imaging of formations downhole, a set of instructions, that, when executed, perform multi-dimensional fluorescence spectrum measurements downhole.

One embodiment provides a downhole apparatus comprising a downhole lab module, the downhole lab module comprising a sample flow line, a sample cell in fluid communication with the sample flow line, the sample cell comprising at least one optical window, a tunable light source adjacent to the sample cell, a spectrometer for detecting fluorescence, a set of instructions, that, when executed, perform multi-dimensional fluorescence spectrum measurements downhole. The apparatus may further comprise an optical filter between the spectrometer and the at least one optical window.

Additional advantages and novel features will be set forth in the description which follows or may be learned by those skilled in the art through reading these materials or practicing the principles described herein. Some of the advantages described herein may be achieved through the means recited in the attached claims.

BRIEF DESCRIPTION OF THE DRAWINGS

The accompanying drawings illustrate certain embodiments and are a part of the specification. Together with the following description, the drawings demonstrate and explain some of the principles of the present invention.

FIG. 6A illustrates a transmission configuration.

FIG. 6B illustrates a backscatter configuration.

FIG. 7A illustrates a transmission layout.

FIG. 7B illustrates a reflection layout.

FIG. 7C illustrates a fiber bundle layout.

Figure 1:
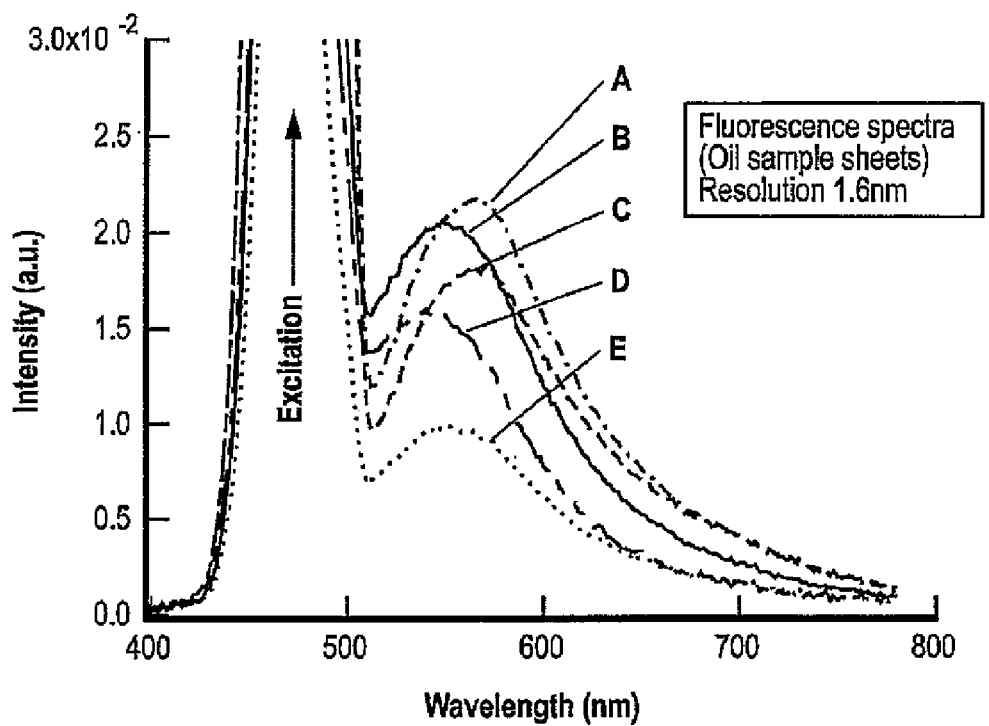
FIG. 1 is a fluorescence spectrum of various crude oils. In the diagram of FIG. 1, a 470 nm LED is used for excitation light.

Throughout the drawings, identical reference numbers and descriptions indicate similar, but not necessarily identical elements. While the principles described herein are susceptible to various modifications and alternative forms, specific embodiments have been shown by way of example in the drawings and will be described in detail herein. However, it should be understood that the invention is not intended to be limited to the particular forms disclosed. Rather, the invention includes all modifications, equivalents and alternatives falling within the scope of the appended claims

DETAILED DESCRIPTION

Illustrative embodiments and aspects of the invention are described below. It will of course be appreciated that in the development of any such actual embodiment, numerous implementation-specific decisions must be made to achieve the developers' specific goals, such as compliance with system-related and business-related constraints, that will vary from one implementation to another. Moreover, it will be appreciated that such a development effort might be complex and time-consuming, but would nevertheless be a routine undertaking for those of ordinary skill in the art having the benefit of this disclosure.

Reference throughout the specification to "one embodiment," "an embodiment," "some embodiments," "one aspect," "an aspect," or "some aspects" means that a particular feature, structure, method, or characteristic described in connection with the embodiment or aspect is included in at least one embodiment of the present invention. Thus, the appearance of the phrases "in one embodiment" or "in an embodiment" or "in some embodiments" in various places throughout the specification are not necessarily all referring to the same embodiment. Furthermore, the particular features, structures, methods, or characteristics may be combined in any suitable manner in one or more embodiments. The words "including" and "having" shall have the same meaning as the word "comprising."

Moreover, inventive aspects lie in less than all features of a single disclosed embodiment. Thus, the claims following the Detailed Description are hereby expressly incorporated into this Detailed Description, with each claim standing on its own as a separate embodiment of this invention.

A fluorescence (FL) spectrum reflects energy structure that is determined by bonds between atoms in a molecule. Fluorescence measurement is often used in the chemical analysis field. In order to observe a fluorescence spectrum, an energy state excitation is necessary. Fluorescence light is emitted during the relaxation process from an excitation state to a ground state.

FIG. 1 shows fluorescence spectra of various crude oils labeled A-E. The large, truncated peak in FIG. 1 represents excitation light that happens to be 470 nm blue LED light. The broader peaks A-E in the 500-600 nm wavelength regions represent fluorescence signals. As illustrated in FIG. 1, different crude oil samples have different spectral shapes at the longer wavelength ranges (as opposed to the nearly identical peak shapes at the excitation light wavelength). However, it is currently difficult to obtain much useful or detailed information about the crude oils based on the fluorescence spectra alone because of the simplicity of the shapes associated with the fluorescence spectra that are excited by certain excitation light sources.

Figure 2:
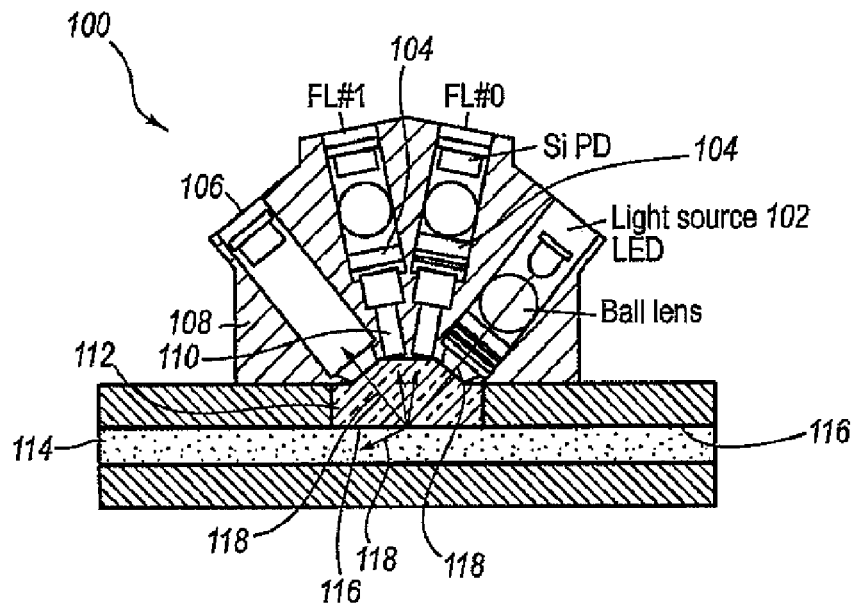
FIG. 2 is a cut-away cross-sectional view of a composition fluid analyzer (CFA) fluorescence detector according to one embodiment.

CFAs have been implemented for fluorescence measurement, but the excitation wavelength is typically a single wavelength and only two emission wavelengths are currently detected. FIG. 2 is a schematic drawing of one fluorescence detector 100 that may be part of a downhole tool (e.g. a downhole wireline tool) that may be used to make fluorescence measurements. The fluorescence detector 100 includes a light source, for example a 470 nm LED light source 102. The fluorescence detector 100 may also include two fluorescence detection channels FL#0 and FL#1 that have different cutoff optical filters 104. The fluorescence detector 100 may also include a reflected light detection channel 106. The channels FL#0, FL#1, and reflected light detection channel 106 may be arranged in an optical prism such as a sapphire prism 108. Each channel (FL#0, FL#1, and reflected light detection channel 106) may include an optical rod such as a glass rod 110 to direct light from an optical window 112 adjacent a sample 114.

In the embodiment of FIG. 2, fluorescence detection channels FL#0 and FL#1 of a downhole testing tool may have $\lambda_1$ and $\lambda_2$ cutoff wavelength optical filters 104, respectively. However, other optical filters may also be used, including additional detection channels. The fluorescence detection channels FL#0 and FL#1 may be used to observe rough spectrum shapes (such as the ones shown in FIG. 1). In one embodiment, the first fluorescence detection channel FL#0 integrates intensity of fluorescence spectrum from $\lambda_1$ and longer, and the second fluorescence detection channel FL#1 integrates intensity of fluorescence above $\lambda_2$. The intensity of the light reflected at an interface 116 between bottom window 112 and a flow line 116 carrying the sample 114 depends on the refractive index of the sample 114 in the flow line 116. However, approximately 100% of the light (represented by arrows 118) from the $\lambda$ emission LED light source 102 is reflected when air flows in the flow line 116 adjacent the window 112. Less than 100% of the light from the $\lambda$ LED light source 102 is reflected if fluid flows through flow line 116.

As mentioned above, fluorescence spectroscopy (1D or one dimension) has been used to get general—but not detailed—information about formation fluids and other downhole fluids (e.g. drilling muds) based on the spectral shapes measured. However, according to some embodiments, more than 1D fluorescence spectroscopy, for example at least 2D fluorescence measurements, may be taken to further characterize formations, downhole fluids, formation fluids, etc. (and such measurements and characterization may be done downhole or in situ). Mud itself does not exhibit fluorescence. Therefore, finding fluorescence in a mud fluid may indicate that oil-bearing formations have been reached.

Figure 3A:
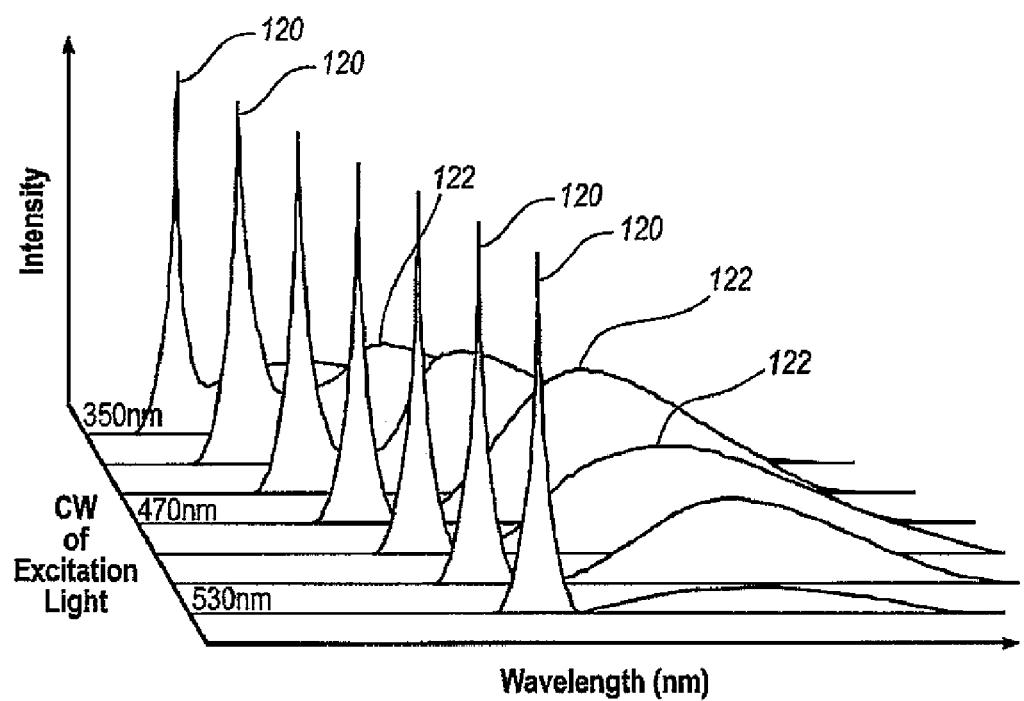
FIG. 3A is a fluorescence spectrum of oil at different excitations of light according to one embodiment.
Figure 3B:
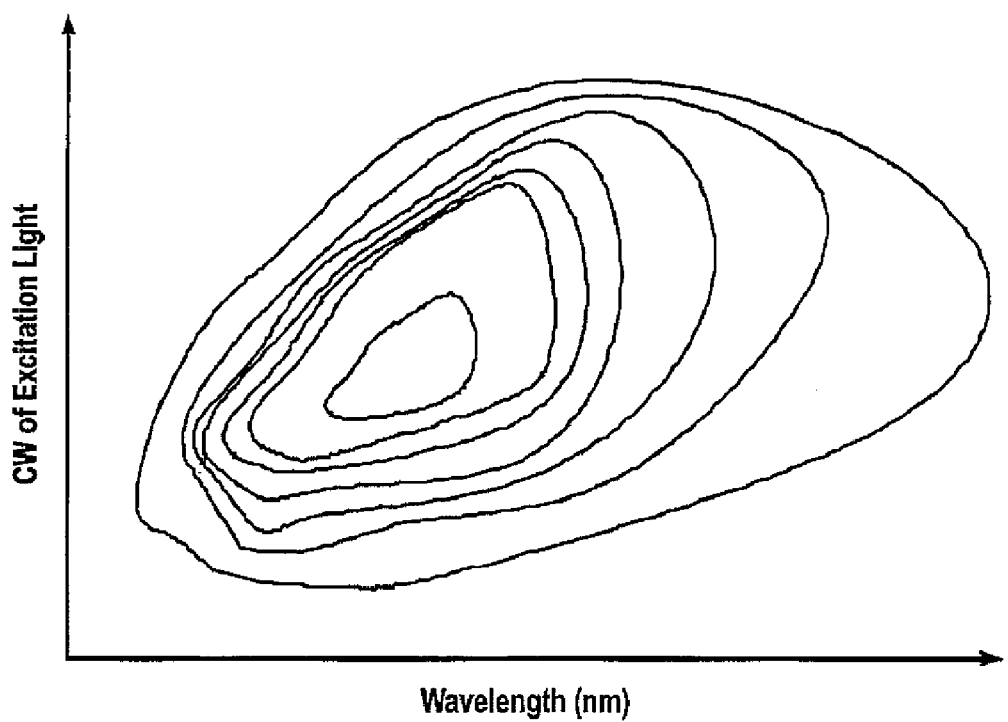
FIG. 3B is a contour plot of the fluorescence spectra shown in FIG. 3A.
Figure 4A:
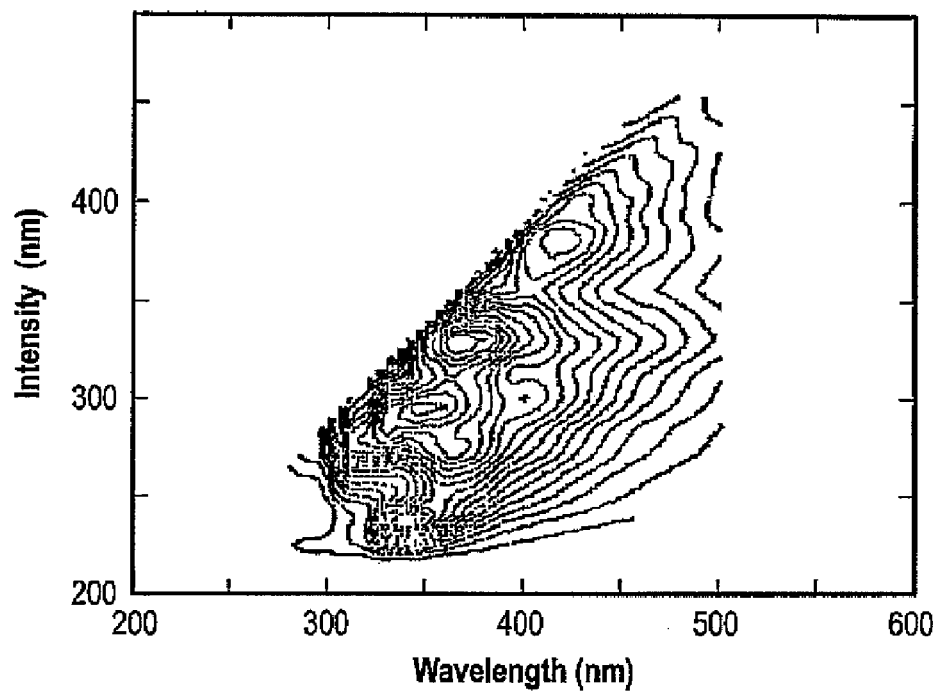
FIG. 4A illustrates a contour plot of an actual oil sample fluorescence spectra for a dead crude oil generated in a lab according to the prior art.
Figure 4B:
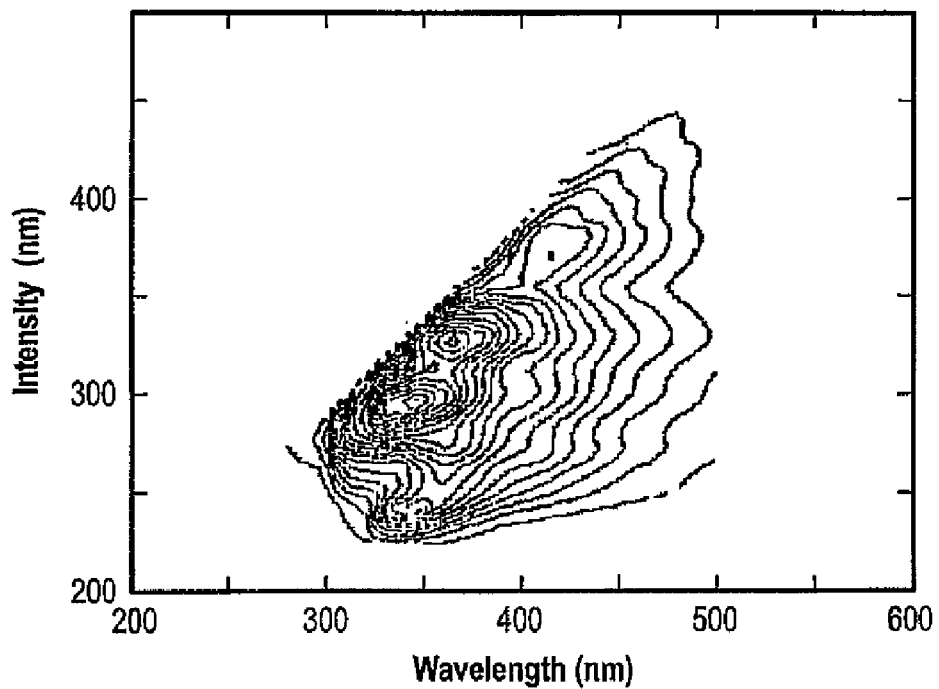
FIG. 4B illustrates a contour plot of an actual oil sample fluorescence spectra for another dead crude oil generated in a lab according to the prior art.

In one embodiment illustrated in FIGS. 3A-3B, a 2D measurement of spectrum vs. wavelength of excitation light is shown. FIG. 3A illustrates fluorescence spectra for different excitation light sources. Sharp peaks 120 in shorter wavelength locations again represent spectra of excitation light. Broader peaks 122 at the longer wavelengths represent fluorescence spectra for the sample (e.g. oil). In one aspect, many fluorescence spectra may be measured with many kinds of excitation light to generate a 2D fluorescence spectrum contour plot such as the one shown in FIG. 3B. FIGS. 4A-4B represent fluorescence measurement data or contour plots from actual dead crude oils that were generated in an uphole lab according to the prior art. FIG. 4A is a 2D spectrum of Sahara crude oil, and FIG. 4B is a 2D spectrum of Nigeria light crude oil. As shown in FIGS. 4A-4B, different samples (such as different oils) exhibit different fluorescence spectrum in uphole labs. In particular, FIGS. 4A-4B illustrate contour plots of dead oil from a tanker spill. Fujita, M., "Analysis and Identification of Spilled Oil in Ocean," JAPAN ENVIRONMENTAL MEASUREMENT & CHEMICAL ANALYSIS, Vol. 19, No. 4, 1990 (rough translation of titles from Japanese). As understood by those of ordinary skill in the art having the benefit of this disclosure, a dead oil is one that is no longer pressurized but has been subjected to atmospheric pressure. Further, one of ordinary skill in the art having the benefit of this disclosure will understand that the volatile fraction of a dead oil will have evaporated from the liquid phase. However, according to principles described herein, different 2D fluorescence spectra are generated downhole, and can be compared to known measurements to identify or characterize the samples downhole. Fluorescence may be of particular interest for the characterization of the aromatic fraction of oil. Part of the aromatic compounds can be quite volatile under atmospheric pressure conditions. With the direct implementation downhole according to principles described herein, the aromatic fraction of a live oil is characterized downhole in one embodiment and would otherwise be lost if the sample was depressurized (as with a tanker spill).

Figure 5A:
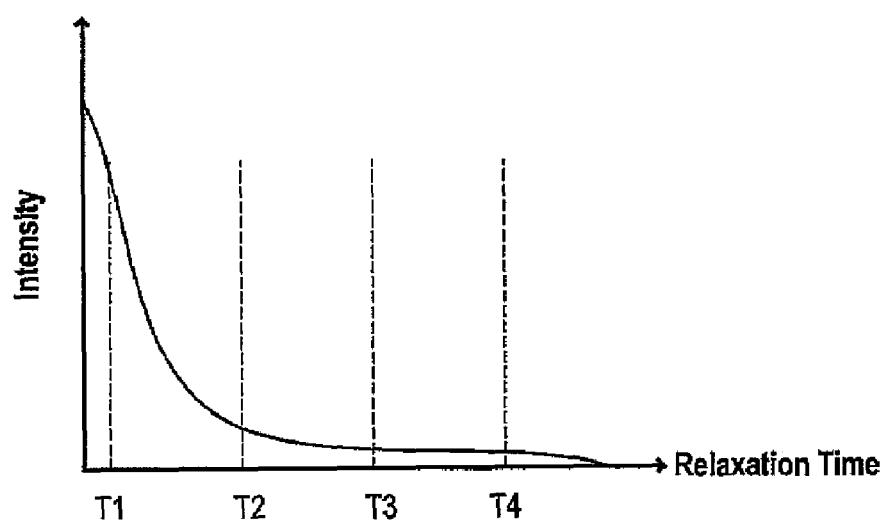
FIGS. 5A-5C illustrate a 2D fluorescence measurement concept of spectrum vs. relaxation time according to one embodiment.
Figure 5B:
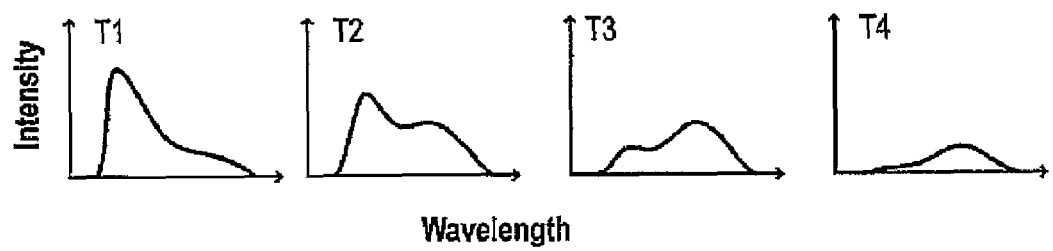
Figure 5C:
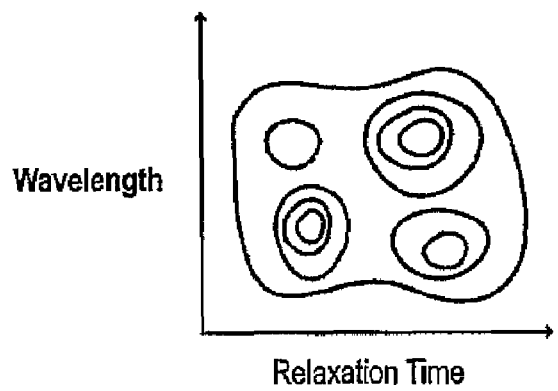

Other at least 2D fluorescence measurements may also be used to characterize samples. For example, FIGS. 5A-5C illustrate 2D fluorescence measurements of a spectrum as a function of relaxation time. Generally, fluorescence "relaxes" over time and fluorescent intensity decreases exponentially with time. FIG. 5A illustrates a typical fluorescence intensity plot over time. Moreover, the fluorescence spectrum shape changes over time. FIG. 5B represents different fluorescence spectra at each of four different times (T1, T2, T3, and T4). The changes in fluorescence spectra over time are characteristic of particular sample compositions that can be recorded and compared to the same criteria of known samples. Thus, the 2D fluorescence spectrum including fluorescence spectrum and the relaxation time axes shows the relaxation process from an excited energy state and is identifiable for different samples. FIG. 5C is a 2D fluorescence spectrum plot showing fluorescence spectrum as a function of relaxation time. The relaxation spectra in the 2D plot of FIG. 5C illustrates a relaxation process that includes features that may be unique to sample compositions (such as different crude oils).

In addition to or separate from using 2D fluorescence measurements to identify samples, some aspect may simply "fingerprint" samples. For example, in one aspect, 2D fluorescence measurements are taken for a first downhole sample in a first borehole. Another set of 2D fluorescence measurements may be taken for a second sample in a second borehole. The 2D fluorescence measurements or "fingerprint" of the first sample may be compared to the "fingerprint" of the second sample to evaluate formation connectivity. For example, if a 2D fluorescence spectrum of crude oil in one formation indicates the same 2D fluorescence spectrum in another formation, it is likely that the formations are connected somewhere.

Figure 6A:
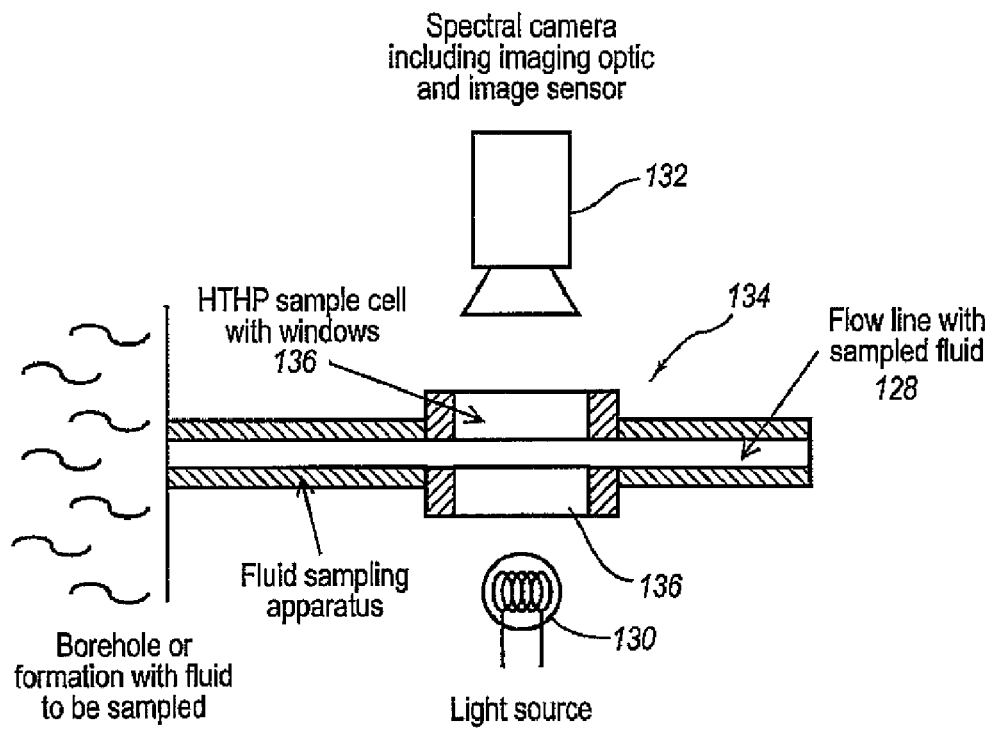
FIG. 6A is a schematic diagram showing an optical layout of a downhole flow line imaging apparatus.
Figure 6B:
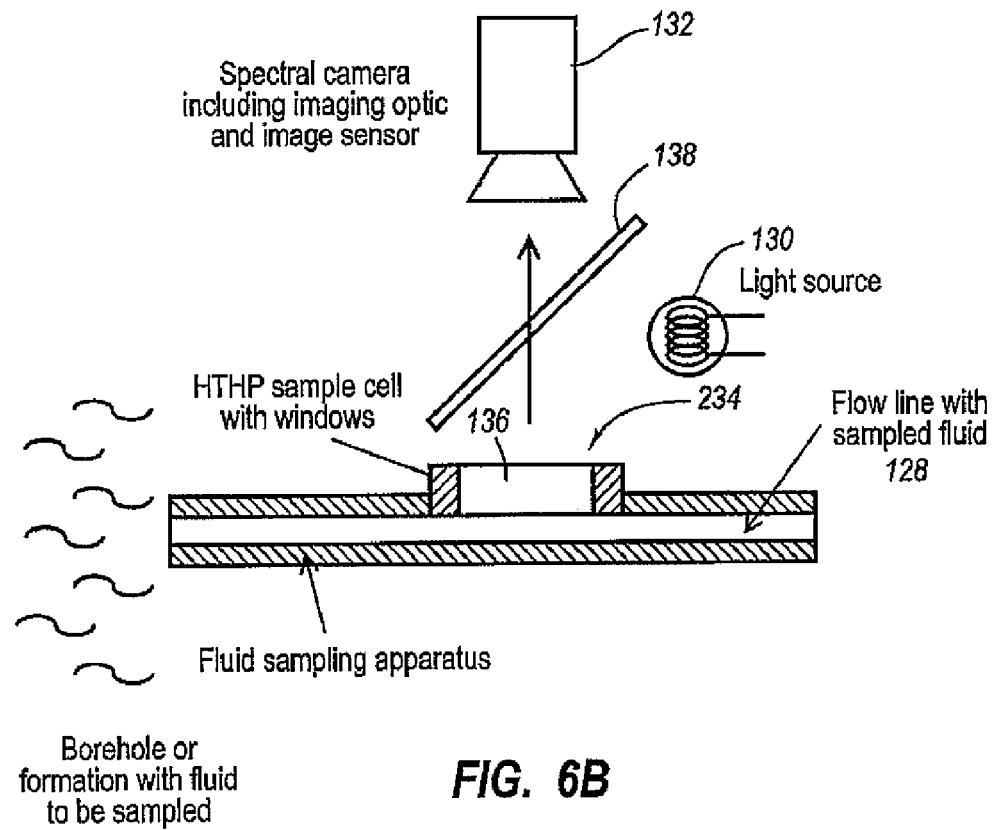
FIG. 6B is another schematic diagram showing an optical layout of a downhole flow line imaging apparatus.

Further, in addition to the two different 2D fluorescence measurements that may be taken, for example, downhole by a downhole tool and relayed uphole, other imaging downhole is also contemplated. FIGS. 6A and 6B illustrate optical layouts of downhole tools having flow line imaging capability according to some embodiments. FIG. 6A is a transmission configuration wherein light from a light source 130 or fluorescence from a sample in a flow line 128 is imaged by a camera 132 (which may be a CCD (charged coupled device), a CMOS (complementary metal oxide semiconductor) camera, or other camera). In the embodiment of FIG. 6A, the light source 130 and the camera 132 are placed on opposite sides of a flow line sample cell 134 having windows 136. The sample cell 134 is fluidly connected to the flow line 128. The sample cell 134 comprises the one or more window 136 shown in FIG. 6A. The windows 136 comprise a material that is at least partially transparent to light. The windows 136 may be made, for example, of sapphire. Many possible configurations of the light source 130 and camera 132 are contemplated herein. Two possible configurations are shown in FIGS. 6A-6B. In one embodiment the camera 132 is a spectral camera. The camera 132 can provide spectral information in function of pixels. A backscatter configuration shown and described below in connection with FIG. 6B may provide the same measurements as those described above, but with spatial resolution instead of averaging it within sample volume.

In a backscatter imaging configuration as shown in FIG. 6B, the light source 130 and the camera 132 may both be arranged on the same side of a sample cell 234. The sample cell 234 may thus include only one window 136. A beam splitter 138, which is shown as a tilted plate between the sample cell 234 and the camera 132, is used to direct light to the sample cell 234 while also allowing backscattered light to return to the camera 132. Accordingly, direct electromagnetic radiation from the light source 130 is directed to the window 136 by the beam splitter 138, and radiation may be reflected from the sample and detected by the camera 132. Reflected light may also be due to light reemitted by the sample in the flow line 128 itself because of fluorescence.

Figure 7A:
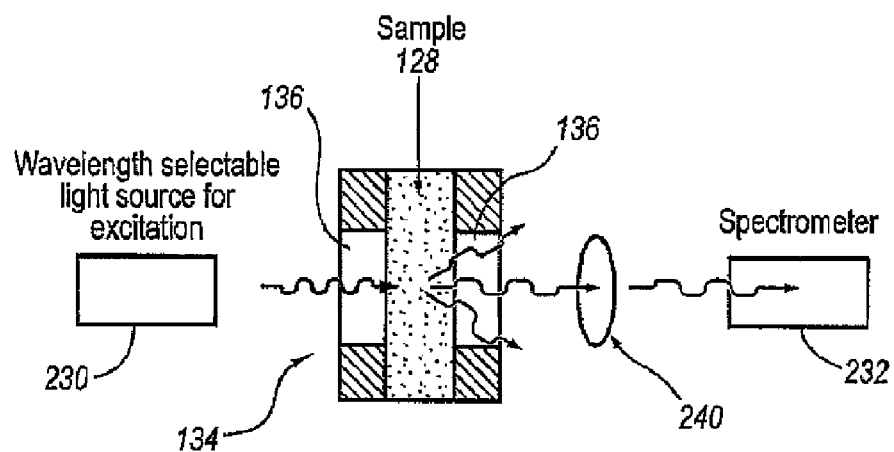
FIG. 7A is a schematic optical layout for optical fluorescent measurement in a flow line according to one embodiment.
Figure 7B:
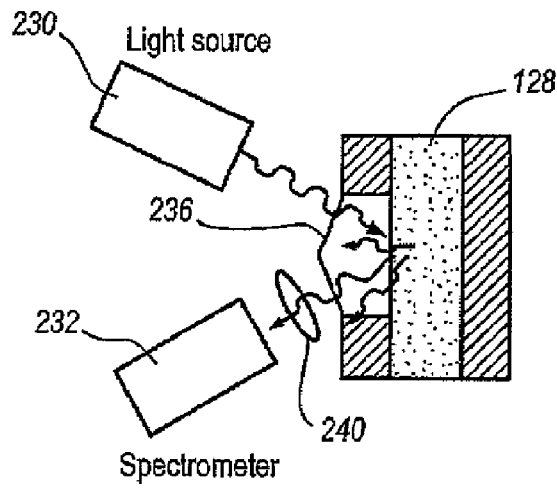
FIG. 7B is a schematic optical layout for optical fluorescent measurement of a formation fluid according to another embodiment.
Figure 7C:
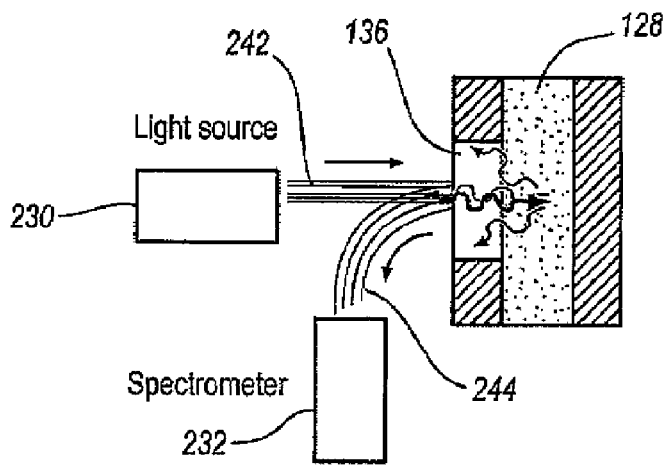
FIG. 7C is a schematic optical layout for optical fluorescent measurement of a formation fluid according to another embodiment.

FIG. 7A illustrates an embodiment wherein a wavelength selectable light source 230 for excitation is arranged on one side of a sample flow line 128 and a lens 240 is arranged between the sample flow line 128 and a spectrometer 232 opposite of the light source 230. FIGS. 7A-7C illustrate several possible apparatuses that may be used for the 2D FL measurement. FIG. 7A illustrates a measurement in a transmission configuration. FIGS. 7B and 7C illustrate mechanisms for measurement in reflection configurations. In FIG. 7A, the excitation light is provided by light source 230, transmitted through the sample 128, and through optical windows 136. A lens system 240 collects the light transmitted through the optical cell 134 and transmits it to the spectrometer 232. In FIG. 7B, the scheme is the same but the analyzed light is one reflected from the cell via window 236. In FIG. 7C, instead of using a lens system to guide the light, an optical fiber 242 is used.

According to some aspects, fluorescence imaging may be used to discriminate between oil-bearing formations and other formations. For example, limestone containing oil will emit fluorescent light following excitation, which can be viewed by a camera, while other formations that do not bear hydrocarbons will tend not to emit any fluorescence. Some of the embodiments that may be used to image fluorescence downhole and help determine which formations contain hydrocarbons are depicted in FIGS. 7B-7C.

FIG. 7B schematically illustrates an apparatus wherein the sample 128 is a formation fluid sample. An optical window 236 may be directly adjacent to or even attached to the formation of interest. A light source such as the wavelength selectable light source 230 emits light through the optical window 236 at an angle and excites the formation fluid 128 and/or any oil in the formation fluid 128. If there is oil in the formation fluid 128, fluorescent light is emitted as the oil relaxes from the excited state. Fluorescence (if any) is directed back through the optical window toward a camera or spectrometer 232 where it is detected or imaged. A lens 240 may focus fluorescence to the spectrometer 232. Accordingly, fluorescence may be viewed or detected uphole via the downhole system illustrated in FIG. 7B to help determine whether formations of interest are hydrocarbon-bearing. In some aspects the downhole system illustrated in FIG. 7B may be used to also determine the composition of any hydrocarbons.

FIG. 7C schematically illustrates another downhole apparatus wherein the sample 128 is a formation fluid. According to the embodiment of FIG. 7C, the optical window 136 is adjacent to or attached to the formation and also coupled to fiber optic bundles 242 and 244. The first fiber optic bundle 242 is optically coupled between the wavelength selectable light source 230 and the optical window 136. The light source 230 emits light through the optical window 136 via the first fiber optic bundle 242 and excites the formation fluid 128 and/or any oil in the formation fluid 128. If there is oil in the formation fluid 128, fluorescent light is emitted as the oil relaxes from the excited state. Fluorescence (if any) is directed back through the optical window and to the camera or spectrometer 232 via the second fiber optic bundle 244 where it is detected or imaged. Again, fluorescence may be viewed or detected uphole via the downhole system illustrated in FIG. 7C to help determine whether formations of interest are hydrocarbon-bearing. Other configurations including a downhole excitation source and a downhole detector may also be used.

Accordingly, in one aspect a method may be implemented which includes providing a downhole testing tool, deploying the downhole testing tool into a borehole, and performing a multi-dimensional fluorescence spectrum measurement downhole. In one aspect two of the multi-dimensional fluorescence spectrum measurements comprise wavelength of excitation light and fluorescence spectrum. Performing the multi-dimensional fluorescence spectrum measurement may comprise plotting wavelength of excitation light versus fluorescence spectrum.

In one aspect, two of the multi-dimensional fluorescence spectrum measurements comprise fluorescence relaxation time and fluorescence spectrum. Performing a multi-dimensional fluorescence spectrum measurement may comprise plotting fluorescence relaxation time versus fluorescence spectrum. In one aspect, performing the multi-dimensional fluorescence spectrum measurement comprises two dimensional fluorescence imaging with a charged-coupled device (CCD) or a complementary metal oxide semiconductor (CMOS) camera.

In one aspect, the method includes communicating the multi-dimensional fluorescence spectrum measurements uphole. The methods may include performing multi-dimensional fluorescence spectrum measurements downhole at multiple boreholes, comparing the multi-dimensional fluorescence spectrum measurements at the multiple boreholes, and determining connectivity between the multiple boreholes based on the comparing of the multi-dimensional fluorescence spectrum measurements. Moreover, in one embodiment the downhole testing tool (which may be a wireline tool) shown in part in FIGS. 2 and 6A-7A further comprises a pressure-volume control unit. Further, in one embodiment the downhole testing tool is permanently installed downhole and in fluid communication with a production line.

Figure 8A:
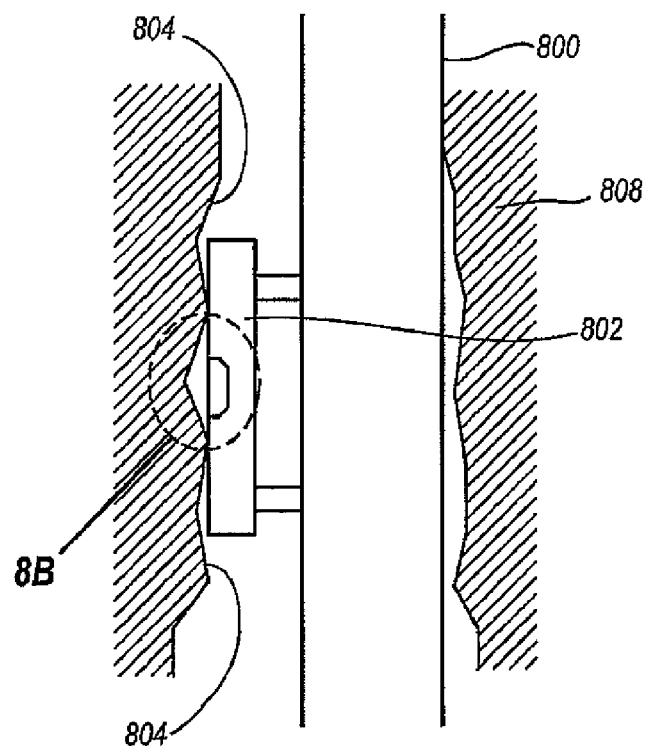
FIG. 8A is a schematic of an apparatus for downhole optical fluorescent measurement at a formation surface according to one embodiment.
Figure 8B:
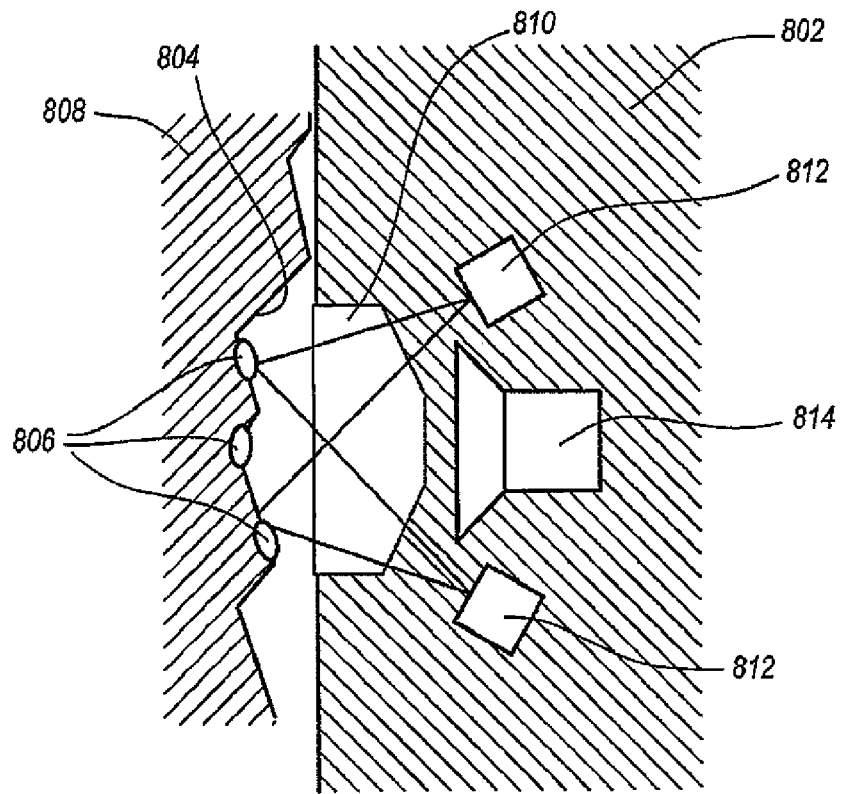
FIG. 8B is a magnified detail schematic of the apparatus of FIG. 8A.

Turning now to FIGS. 8A-8B, another configuration that may be used for 2D fluorescent imaging is shown. According to the embodiment of FIGS. 8A-8B, a downhole tool 800 may include an extendable pad 802 enabling characterization of fluids 806 at a formation surface 804. The pad 802 may be pushed or pumped out to remove the mud cake and establish optical contact with the surface 804 of the formation 808. A window 810 interfaces between the formation 808 and the inside of the downhole tool 800 (which may be fluorescence measurement capable as described above). Light sources 812 excite the formation 808 and any fluids or oils 806 at the surface 804. A spectral camera 814 behind the window 810 performs the imaging, such as fluorescence imaging, and facilitates fluid characterization in accordance with principles described above.

Figure 9A:
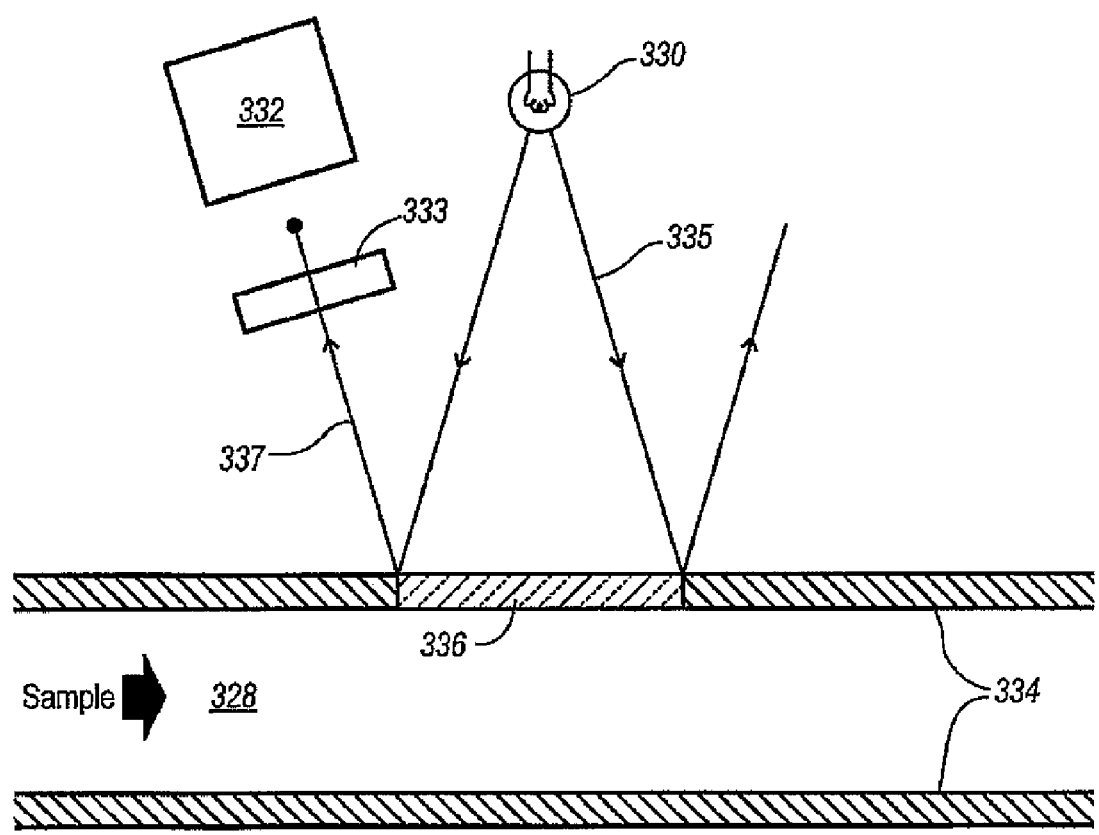
FIG. 9A is another schematic diagram showing an optical layout of a downhole flow line fluorescence detection apparatus utilizing a tunable or pulsed light source.
Figure 9B:
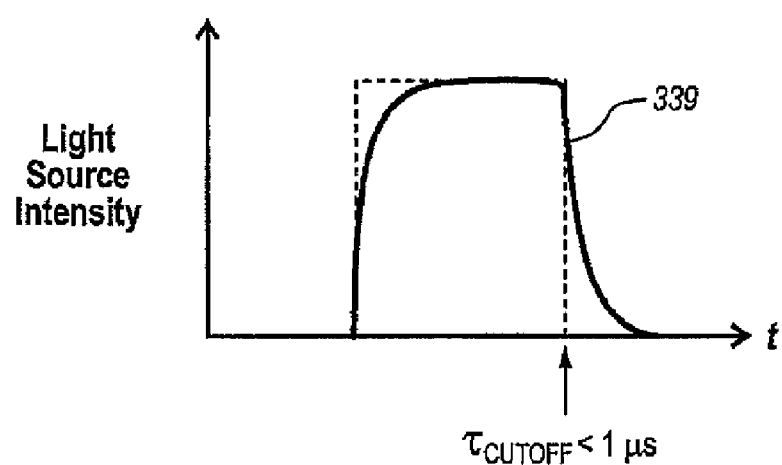
FIG. 9B illustrates a plot of fluorescence intensity or relaxation as a function of time according to use of the apparatus of FIG. 9A.

FIGS. 9A-9D illustrate apparatus and plots associated with some embodiments. Referring to FIG. 9A, one apparatus that may be used to measure fluorescence downhole is shown. Similar to the embodiment of FIGS. 6A-6B, FIG. 9A illustrates a schematic optical layout of a downhole tool having flow line imaging capability. In FIG. 9A fluorescence acquisition is collected by a spectrometer 332. Excitation light 335 from a light source 330 excites a sample 328 in a flow line 334 through an optical window 336. In the imaging configuration shown in FIG. 9A, the light source 330 and the spectrometer 332 may both be arranged on the same side of the optical window 336. Fluorescent light 337 resulting from the excitation light 335 is emitted from the sample 328 and detected by the spectrometer 332.

Figure 9C:
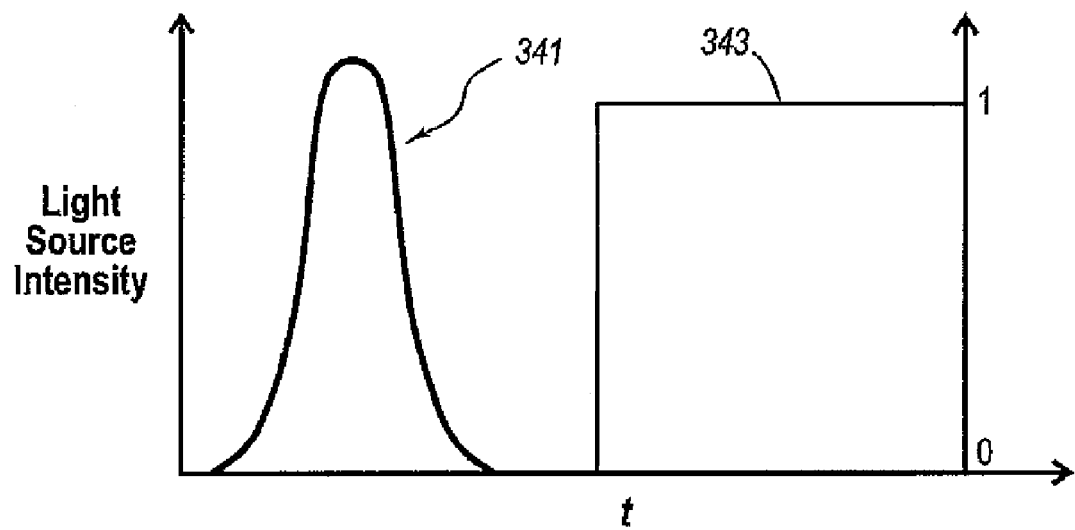
FIG. 9C illustrates a plot of light source intensity as a function of time when an optical filter is used with the apparatus of FIG. 9A.
Figure 9D:
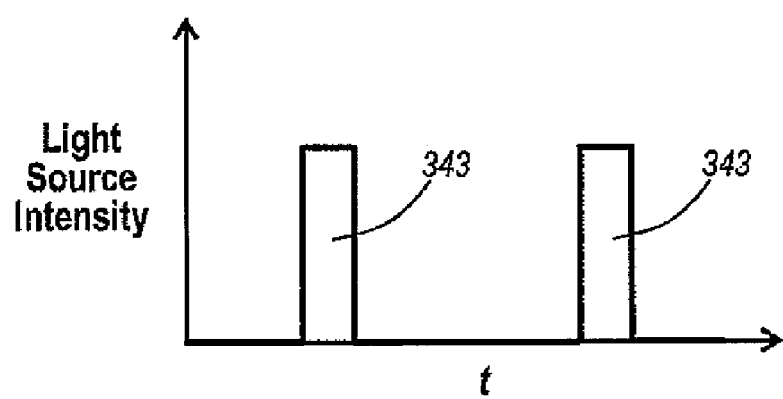
FIG. 9D illustrates a light pulse for the light source of FIG. 9A according to one embodiment.

The light source 330 may comprise a tunable light source, and it may also comprise a pulsed light source. A pulsed light source may have an intensity vs. time plot shown in FIG. 9B wherein light intensity 339 drops off when the light is pulsed at a cutoff time $\tau_{cutoff}$. $\tau_{cutoff}$ may be less than 1 μs. FIG. 9D illustrates light pluses 343 from the source 330 according to one embodiment.

In some embodiments, the apparatus of FIG. 9A may include an optical filter between the optical window 336 and the spectrometer 332. For example, as shown in FIG. 9A, a long pass optical filter 333 (e.g. $\lambda_{cutoff}$<1 μm) may be arranged in front of the spectrometer 332. Operation of the apparatus arrangement of FIG. 9A may result in a plot like the one shown in FIG. 9C. As shown in FIG. 9C, activation of the light source 330 results in an excitation light spike 341. The excitation light is turned off or pulsed, and fluorescent light from the sample 328 (FIG. 9A) continues to be detected by the spectrometer 332 (FIG. 9A), but fluorescence transmission to the spectrometer 332 (FIG. 9A) may be limited by the long pass filter 333. The apparatus of FIG. 9A may be used according to principles described herein to generate fluorescence measurements and help characterize or identify downhole samples.

The preceding description has been presented only to illustrate and describe certain embodiment and aspects. It is not intended to be exhaustive or to limit the invention to any precise form disclosed. Many modifications and variations are possible in light of the above teaching. Moreover, the principles described herein are applicable to drilling and measurement operations, production logging, permanent monitoring, well services for injected fluid, etc.

The embodiments and aspects were chosen and described in order to best explain the principles of the invention and its practical application. The preceding description is intended to enable others skilled in the art to best utilize the principles described herein in various embodiments and with various modifications as are suited to the particular use contemplated. It is intended that the scope of the invention be defined by the following claims.

What is claimed is:

1. A method, comprising:
providing a downhole testing tool, wherein the downhole testing tool comprises a downhole detector with a pulsed blue semiconductor light source;
deploying the downhole testing tool into a borehole;
performing a multi-dimensional fluorescence spectrum measurement downhole,
wherein two of the multi-dimensional fluorescence spectrum measurements comprise fluorescence relaxation time and fluorescence spectrum, and
wherein the pulsed blue semiconductor light source is used to measure the fluorescence relaxation time.

2. A method according to claim 1, wherein two of the multi-dimensional fluorescence spectrum measurements comprise wavelength of excitation light and fluorescence spectrum.

3. A method according to claim 2, wherein the performing a multi-dimensional fluorescence spectrum measurement comprises plotting wavelength of excitation light versus fluorescence spectrum.

4. A method according to claim 1, wherein the multi-dimensional fluorescence spectrum measurements comprise characterization of an aromatic fraction of a live oil.

5. A method according to claim 1, wherein the performing a multi-dimensional fluorescence spectrum measurement comprises plotting fluorescence relaxation time versus fluorescence spectrum.

6. A method according to claim 1, wherein the performing the multi-dimensional fluorescence spectrum measurement comprises two dimensional fluorescence imaging with a charged-coupled device (CCD) or a complementary metal oxide semiconductor (CMOS) camera.

7. A method according to claim 1, further comprising communicating the multi-dimensional fluorescence spectrum measurement uphole.

8. A method according to claim 1, further comprising:
performing the multi-dimensional fluorescence spectrum measurement downhole at multiple boreholes;
comparing the multi-dimensional fluorescence spectrum measurements at the multiple boreholes;
determining connectivity between the multiple boreholes based on the comparing of the multi-dimensional fluorescence spectrum measurements.

9. A method according to claim 1, wherein the downhole testing tool further comprises a pressure-volume control unit.

10. A method according to claim 1, wherein the downhole testing tool comprises a portion of a wireline tool.

11. A method according to claim 1, wherein the downhole testing tool is permanently installed downhole and in fluid communication with a production line.

12. A method according to claim 1, further comprising performing a multi-dimensional fluorescence spectrum measurement in a lab of a same fluid and comparing the multi-dimensional fluorescence spectrum measurement of the lab with multi-dimensional fluorescence spectrum measurement performed downhole.

13. A method according to claim 1, wherein the pulsed blue semiconductor light source is a pulsed blue LED light source.

14. A method of identifying subterranean fluids, comprising:
providing a downhole testing tool, wherein the downhole testing tool comprises a downhole detector with a pulsed blue semiconductor light source in an extendable pad;
deploying the downhole testing tool into a borehole; and
characterizing a fluid sample downhole according to multi-dimensional fluorescence spectrum measurements by using the downhole testing tool,
wherein two of the multi-dimensional fluorescence spectrum measurements comprise fluorescence relaxation time and fluorescence spectrum, and
wherein the pulsed blue semiconductor light source has a cutoff time less than 1 μs to measure the fluorescence relaxation time.

15. A method according to claim 14, wherein two of the multi-dimensional fluorescence spectrum measurements comprise wavelength of excitation light and fluorescence spectrum.

16. A method according to claim 14, wherein the multi-dimensional fluorescence spectrum measurements comprise two dimensional fluorescence imaging with a charged-coupled device (CCD) or a complementary metal oxide semiconductor (CMOS) camera.

17. A method according to claim 16, wherein a light source and the camera comprise a transmission imaging configuration.

18. A method according to claim 16, wherein a light source, a reflector, and the camera comprise a back-scattered imaging configuration.

19. A method according to claim 14, wherein the subterranean fluids comprise one or more of formation fluid and drilling mud.

20. A downhole apparatus, comprising:
a downhole lab module, the downhole lab module comprising:
a sample flow line;

a sample cell in fluid communication with the sample flow line, the sample cell comprising at least one optical window;
a pulsed blue semiconductor light source adjacent to the sample cell;
a spectrometer for detecting fluorescence;
a set of instructions, that, when executed, perform multi-dimensional fluorescence spectrum measurements downhole,
wherein two of the multi-dimensional fluorescence spectrum measurements comprise fluorescence relaxation time and fluorescence spectrum, and
wherein the pulsed blue semiconductor light source is used to measure fluorescence relaxation time.

21. A downhole apparatus according to claim 20, further comprising a set of instructions that, when executed:
excite an energy state of formation fluids adjacent to the optical window above a ground state;
measure fluorescence light emitted by the formation fluids in a relaxation process from an excited state to the ground state;
plot fluorescence spectra as a function of time.

22. A downhole apparatus according to claim 20, further comprising a set of instructions that, when executed:
excite an energy state of formation fluids adjacent to the optical window above a ground state;
measure fluorescence light emitted by the formation fluids in a relaxation process from an excited state to the ground state;
plot wavelength of excitation light versus fluorescence spectrum.

23. A downhole apparatus according to claim 20, further comprising a camera capable of 2D fluorescence imaging of formations downhole.

24. A downhole apparatus, comprising:
a downhole module, the downhole module being extendable to a surface of a downhole formation:
a pulsed semiconductor light source in the downhole module;
a spectrometer for detecting fluorescence emitted from the surface of the formation in the downhole module;
a set of instructions, that, when executed, perform multi-dimensional fluorescence spectrum measurements downhole of the formation,
wherein two of the multi-dimensional fluorescence spectrum measurements comprise fluorescence relaxation time and fluorescence spectrum and
wherein the pulsed blue semiconductor light source has a cutoff time less than 1 µs to measure the fluorescence relaxation time.

* * * * *